United States Patent [19]

Simpson et al.

[11] 4,039,387

[45] Aug. 2, 1977

[54] **MEDIUM AND METHOD FOR DISTINGUISHING *NEISSERIA GONORRHOEAE* AND *NEISSERIA MENINGITIDIS***

[75] Inventors: Lynn B. Simpson, Corning; Milton M. Takeguchi, Painted Post, both of N.Y.

[73] Assignee: Corning Glass Works, Corning, N.Y.

[21] Appl. No.: 701,891

[22] Filed: July 1, 1976

[51] Int. Cl.$^2$ .............................. C12K 1/10; C12K 1/06
[52] U.S. Cl. .............................. 195/100; 195/103.5 M
[58] Field of Search .............................. 195/99–103.5 M

[56] References Cited

PUBLICATIONS

Chemical Abstracts, vol. 75, 59948s, 1971.

Chemical Abstracts, vol. 74, 1456t, 1971.
Chemical Abstracts, vol. 75, 137373, 1971.

*Primary Examiner*—Lionel M. Shapiro
*Assistant Examiner*—Robert J. Warden
*Attorney, Agent, or Firm*—James A. Giblin; Clinton S. Janes, Jr.; Clarence R. Patty, Jr.

[57] ABSTRACT

A microbial growth medium for distinguishing *Neisseria gonorrhoeae* from *Neisseria meningitidis*. The medium comprises a gonococci and meningococci specific medium having incorporated therein a quantity of 8-anilino-1-naphthalene-sulfonic acid (ANS) or a salt thereof, at a concentration sufficient to permit the growth of the meningococci and inhibit the growth of the gonococci.

10 Claims, No Drawings

MEDIUM AND METHOD FOR DISTINGUISHING *NEISSERIA GONORRHOEAE* AND *NEISSERIA MENINGITIDIS*

RELATED PATENT APPLICATION

Patent Application Ser. No. 701,894, "Microbial Medium Having Fluorescent Growth Indicator", filed of even date in the names of C. A. Lepp, R. D. Mason, and W. S. Ramsey and assigned to the present assignee.

BACKGROUND OF THE INVENTION

Field

This disclosure is concerned generally with microbial growth media and specifically with a modified gonococci and meningococci specific medium useful for distinguishing the two species of *Neisseria*.

Prior Art

A major concern of the clinical microbiology laboratory is to rapidly and accurately provide the clinician with information concerning the presence or absence of specific pathogenic bacteria. The importance of rapidly and accurately identifying *Neisseria gonorrhoeae* and *Neisseria meningitidis* is well recognized. To do this, bacteria from a clinical specimen must be isolated and then identified.

The identification of *N. gonorrhoeae* and *N. meningitidis* commonly consists of two steps, a presumptive identification step and then a definitive identification. The first step requires the use of a gonococci and meningococci specific medium. A gonococci and meningococci-specific growth medium is a medium in which are incorporated antimicrobial agents (such as 3ug vancomycin, 7.5ug colistin, 12.5 units nystatin, 1 ug amphotericin B, and 3 ug trimethoprim lactate per ml of medium) which permit the growth of *N. gonorrhoeae* and of *N. meningitidis* and inhibit the growth of almost all other bacteria. Thayer-Martin medium (see Thayer, J. D. and Martin, J. E., "Improved Medium Selective for Cultivation of *N. gonorrhoeae* and *N. meningitidis*", Pub. Health Rep. 81:559–562:1966) and NYC medium (see Faur, Y. C., Weisburd, M. H., Wilson, M. E., and May, P. S., "A New Medium for the Isolation of Pathogenic Neisseria (NYC Medium)", Health Lab. Sci. 10: 44–74, 1973) are examples of this type of medium.

The following table shows the compositions of these two media:

TABLE I

Composition of Thayer-Martin Medium & NYC Medium

| Thayer-Martin | Per 200 ml | NYC | Per 200 ml |
|---|---|---|---|
| GC Medium Base | 100 ml | NYC Basal Medium | 128 ml |
| IsoVitaleX enrich. | 2 ml | Horse plasma | 24 ml |
| VCN inhibitor | 2 ml | 3% hemolyzed horse red blood cells | 40 ml |
| Hemoglobin, 2% aqueous | 100 ml | 50g % glucose solution | 2 ml |
| | | Yeast dialysate | 5 ml |
| | | Antibiotic mixture | 1 ml |

The major differences between these 2 media are the antibiotic content and the ingredients used for nutritional enrichment. Thayer-Martin contains 3 antibiotics (vancomycin, colistin, & nystatin), and contains IsoVitaleX and hemoglobin for nutritional enrichment. NYC medium contains 4 antibiotics (vancomycin, colistin, amphotericin B, and trimethoprim lactate), and contains horse plasma, hemolyzed horse red blood cells, glucose, and yeast dialysate for nutritional enrichment.

After a specific medium is chosen, a presumptive i.d. step is taken.

Presumptive i.d.:

Clinical specimens suspected of containing gonococci or meningococci are inoculated onto the medium which is selective for gonococci and meningococci. The ability to grow on the specific medium distinguishes the two Neisseria bacteria from practically all other bacteria. Thus, Gram-negative, oxidase-positive diplococci found to grow on a Thayer-Martin (or TM) medium is deemed to constitute a presumptive identification for either or both of the above-named Neisseria species. A non-selective medium such as blood agar may also be inoculated with a portion of the same clinical specimen to examine for pathogenic bacteria inhibited by the specific medium.

Definitive i.d.

A definitive identification requires that the identity of the organism be established beyond question. It is known that carbohydrate fermentation tests or fluorescent antibody staining can be used to confirm the presumptive identification and to definitively identify the gonococci and meningococci. Unfortunately, carbohydrate fermentation tests tend to be expensive, are unreliable, and require about 24 to 48 hours. Although a more rapid fermentation method is available, it still requires an incubation period and has disadvantages similar to the less rapid conventional fermentation tests. The fluorescent antibody test is rapid but sensitivity and specificity problems are commonly encountered.

Surprisingly, we have now found that many of the above disadvantages can be avoided or minimized by using a slightly modified meningococci and gonococci specific medium. Our discovery allows the definitive identification of *N. gonorrhoeae* and *N. meningitidis* without additional technical manipulations or incubation beyond the initial isolation on the modified medium specific to the two species. Details of our medium and various ways of using it are described herein.

SUMMARY OF THE INVENTION

Our microbial medium useful for distinguishing *Neisseria gonorrhoeae* from *N. meningitidis* comprises a gonococci and meningococci specific medium having incorporated therein 8-anilino-1-naphthalene-sulfonic acid (ANS), or a salt thereof, in a quantity sufficient to permit the growth of the meningococci bacteria and inhibit the growth of the gonococci bacteria. Especially preferred gonococci and meningococci specific media include a Thayer-Martin type medium and a NYC-type medium containing at least about 0.5 mg/ml and 0.08 mg/ml, respectively, of the ANS, preferably in the form of a salt (e.g. sodium, magnesium, potassium ammonium).

Our method for the definitive identification of *N. gonorrhoeae* in a specimen comprises the steps of (A) incubating one portion of the specimen with a meningococci and gonococci specific medium and (B) incubating another portion of the specimen with the medium containing the required amount of ANS to determine whether any microbes grown in step (A) will also grow (or be inhibited) by the incubation of step (B). Steps (A) and (B) may be simultaneous or sequential.

In yet another embodiment, there is provided a media container having three sections: one section containing only the specific-type medium, a second section containing similar specific-type medium having incorporated therein a sufficient amount of the ANS, or salt thereof, to distinguish the two species, and a third section containing a nonspecific medium such as blood agar to isolate bacteria other than gonococci and/or meningococci that may be present in a specimen. In use, all three media would be inoculated with a portion of a given specimen (or colony) and, by noting the growth or no-growth results, a definitive identification for *N. gonorrhoeae* or *N. meningitidis* is provided.

SPECIFIC EMBODIMENTS

Our disclosure is based on the discovery that above a given concentration of ANS or salt thereof in a gonococci and meningococci-specific medium, *N. gonorrhoeae* growth is inhibited where *N. meningitides* growth is not inhibited. Thus, the two species can be distinguished on this basis and a rapid and definitive identification of the Neisseria bacteria is possible. Our method of identification is especially useful in providing a rapid and accurate means of detecting the presence of gonococci in a specimen. Our media and methods of using them are illustrated in the following examples.

EXAMPLE I

The standard Thayer-Martin (TM) medium was used as basal medium. This medium was prepared with GC Medium Base (Difco), to which hemoglobin (Difco), VCN inhibitor (BBL), and IsoVitalex enrichment (BBL) were added to a final 1% concentration (v/v) of each additive. TM medium was prepared containing various concentrations (0, 0.05, 0.08, 0.25, and 0.50 mg/ml) of 8-anilino-1-naphthalene-sulfonic acid, magnesium salt, (ANS, Kodak). Five strains of *N. gonorrhoeae* and four strains of *N. meningitidis* were tested. Suspensions of bacteria were made in sterile GC broth (liquid), which was similar in composition to GC Medium Base, except that agar was omitted to avoid solidification. The bacterial concentration of these suspensions was adjusted to approximately $10^8$ colony-forming units per ml. Each medium was inoculated by dropping 0.05 ml of the suspension on the agar surface. Inoculated media were incubated in 5% $CO_2$ at 35° C for 16–18 hours. The results are shown in Table II where "Gr" indicates growth and "NGr" indicates no growth.

TABLE II
Effect of ANS on Growth of *N. gonorrhoeae* and *N. meningitidis*

| BACTERIA | Thayer-Martin-Type Media Containing ANS conc. (mg/ml) of: | | | | |
|---|---|---|---|---|---|
|  | 0 | 0.05 | 0.08 | 0.25 | 0.50 |
| *N. gonorrhoeae* Strains |  |  |  |  |  |
| 1 | Gr | Gr | Gr | Gr | NGr |
| 2 | Gr | Gr | Gr | Gr | NGr |
| 3 | Gr | Gr | Gr | Gr | NGr |
| 4 | Gr | Gr | Gr | Gr | NGr |
| 5 | Gr | Gr | Gr | Gr | NGr |
| *N. meningitidis* Strains |  |  |  |  |  |
| 1 | Gr | Gr | Gr | Gr | Gr |
| 2 | Gr | Gr | Gr | Gr | Gr |
| 3 | Gr | Gr | Gr | Gr | Gr |
| 4 | Gr | Gr | Gr | Gr | Gr |

As can be seen from the above results, *N. gonorrhoeae* grew on all except the media containing the ANS at a concentration of 0.5 mg/ml of medium. Growth and growth inhibition were very evident when the media were examined under a long wave UV light (340 to 380 nm). Identical results were obtained when these media were inoculated with a cotton-tipped swab containing these bacteria. Hence, it appears clear that the growth characteristic can be used to definitively identify *N. gonorrhoeae* and *N. meningitidis*.

EXAMPLE II

The preceding experiment was repeated with the same gonococcal strains and the same meningococcal strains plus five non-pathogenic *Neisseria* sp., *Candida albicans*, and five enteric bacteria.

TABLE III
Effort of ANS on Growth of Various Bacterial Species on Thayer-Martin (TM) Medium

| Bacteria | TM Medium Containing ANS conc. (mg/ml) of: | | | | |
|---|---|---|---|---|---|
|  | 0 | 0.05 | 0.08 | 0.25 | 0.50 |
| *N. gonorrhoeae* strains 1–5 | Gr | Gr | Gr | Gr | NGr |
| *N. meningitidis* strains 1–4 | Gr | Gr | Gr | Gr | Gr |
| *N. lactamicus* | NGr | NGr | NGr | NGr | NGr |
| *N. sicca* | NGr | NGr | NGr | NGr | NGr |
| *N. flavescens* | NGr | NGr | NGr | NGr | NGr |
| *N. mucosa* | NGr | NGr | NGr | NGr | NGr |
| *C. albicans* | Gr | Gr | Gr | Gr | Gr |
| *P. vulgaris* | Gr | Gr | Gr | Gr | Gr |
| *P. morganii* | Gr | Gr | Gr | Gr | Gr |
| *E. coli* | NGr | NGr | NGr | NGr | NGr |
| *K. pneumoniae* | NGr | NGr | NGr | NGr | NGr |
| *S. sonnei* | NGr | NGr | NGr | NGr | NGr |
| *E. cloacae* | NGr | NGr | NGr | NGr | NGr |

The specificity of the test system was revealed by this experiment. The pathogenic Neisseria, *N. gonorrhoeae* & *N. meningitidis*, were separated from the non-pathogenic Neisseria by growth on Thayer-Martin, and they were distinguished from each other by the growth-no growth characteristics on TM-ANS (0.5 mg/ml). Although *C. albicans* and Proteus also grew on TM-ANS (0.5 mg/ml), these bacteria pose no serious problems as they can easily be differentiated from pathogenic Neisseria by a simple Gram stain.

In subsequent experiments, a new medium which incorporates features of both TM and NYC media was used as basal medium. This medium (named CGW medium) contained GC medium base (Difco), to which 1% IsoVitaleX (Baltimore Biological Labs.), vancomycin (3 ug/ml), colistin (7.5 ug/ml), amphotericin B (1 ug/ml), and trimethoprim lactate (3 ug/ml) were added. This CGW medium waS prepared containing various concentrations (0, 0.05, 0.06, 0.07, 0.08 mg/ml) of 8-anilino-1-naphthalene-sulfonic acid, magnesium salt (ANS, Kodak). Hemoglobin was not incorporated in the medium. Therefore, colonial morphology of bacteria on this clear medium was easily studied. Five strains of *N. gonorrhoeae* and five strains of *N. meningitidis* were tested as before.

TABLE IV
Effect of ANS on *N. gonorrhoeae* & *N. meningitidis* on CGW medium.

| Bacteria | CGW Medium containing ANS conc. (mg/ml) of: | | | | |
|---|---|---|---|---|---|
|  | 0 | 0.05 | 0.06 | 0.07 | 0.08 |
| *N. gonorrhoeae* strains |  |  |  |  |  |
| 2 | Gr | Gr | NGr | NGr | NGr |
| 3 | Gr | Gr | Gr | NGr | NGr |
| 6 | Gr | Gr | NGr | NGr | NGr |
| 7 | Gr | Gr | Gr | NGr | NGr |
| 8 | Gr | Gr | Gr | Gr | NGr |

TABLE IV-continued
Effect of ANS on
N. gonorrhoeae & N. meningitidis on CGW medium.

| Bacteria | CGW Medium containing ANS conc. (mg/ml) of: | | | | |
|---|---|---|---|---|---|
| | 0 | 0.05 | 0.06 | 0.07 | 0.08 |
| N. meningitidis strains | | | | | |
| 1 | Gr | Gr | Gr | Gr | Gr |
| 2 | Gr | Gr | Gr | Gr | Gr |
| 5 | Gr | Gr | Gr | Gr | Gr |
| 6 | Gr | Gr | Gr | Gr | Gr |
| 7 | Gr | Gr | Gr | Gr | Gr |

As can be seen from the above results, N. gonorrhoeae was clearly differentiated from N. meningitidis by the growth-no growth characteristic on CGW medium containing ANS at a concentration of 0.08 mg/ml of medium.

EXAMPLE III

CGW medium containing no ANS and CGW medium containing ANS (0.08 mg/ml) were then tested with 16 gonococcal strains and 22 meningococcal strains.

TABLE V
Gonococcal and Meningococal Differentiation

| Bacteria | CGW | Growth on: CGW-ANS (0.08 mg/ml) |
|---|---|---|
| N. gonorrhoeae strains 2, 3, 7, 8, 9 10, 11, 12, 13, 14 15, 16, 17, 18, 19 | Gr | NGr |
| N. meningitidis Strains 1, 2, 4, 6, 8 9, 10, 11, 12, 13 14, 15, 16, 17, 18 19, 20, 21, 22, 23 24, 25 | Gr | Gr |

The reliability of this test system was again demonstrated in this experiment. All gonococcal strains were differentiated from all meningococcal strains on CGW medium containing an ANS concentration of 0.08 mg/ml of medium.

EXAMPLE IV

Specificity of this system was examined by testing CGW and CGW-ANS (0.08 mg/ml) media with five non-pathogenic Neisseria, Candida albicans, and Proteus vulgaris.

TABLE VI
Specificity of CGW-ANS (0.08 mg/ml) Medium

| Bacteria | Growth on: | |
|---|---|---|
| | CGW | CGW-ANS (0.08 mg/ml) |
| N. catarrhalis | NGr | NGr |
| N. lactamicus | NGr | NGr |
| N. mucosa | NGr | NGr |
| N. subflava | NGr | NGr |
| N. flavescens | NGr | NGr |
| P. vulgaris | NGr | NGr |
| C. albicans | Gr | Gr |

All non-pathogenic Neisseria did not grow on CGW or on CGW-ANS media, thereby separating them from the gonococci and the meningococci. P. vulgaris also did not grow on either media. Although C. albicans grew on both media, it can be easily differentiated from Neisseria by a simple Gram stain.

Further Experiments

Experimental data which may help to explain the different ANS concentrations required in TM and in NYC media are shown below. CGW medium with and without 1% hemoglobin and containing various concentrations of ANS were tested with 2 gonococcal and 2 meningococcal strains.

TABLE VII
Effect of Hemoglobin on
ANS Concentration Required in CGW Medium

| Medium | Growth[1] of: | | | |
|---|---|---|---|---|
| | NG2 | NG8 | NM6 | NM25 |
| CGW-no hemoglobin, with ANS conc. (mg/ml) of: | | | | |
| 0.0 | Gr | Gr | Gr | Gr |
| 0.25 | NGr | NGr | NGr | NGr |
| 0.30 | NGr | NGr | NGr | NGr |
| 0.40 | NGr | NGr | NGr | NGr |
| 0.50 | NGr | NGr | NGr | NGr |
| CGW-1% hemoglobin, with ANS conc. (mg/ml) of: | | | | |
| 0.0 | Gr | Gr | Gr | Gr |
| 0.25 | Gr | Gr | Gr | Gr |
| 0.30 | Gr | Gr | Gr | Gr |
| 0.40 | NGr | NGr | Gr | Gr |
| 0.50 | NGr | NGr | Gr | Gr |

[1]NG2, NG8 = gonococcal strains 2 & 8
NM6, NM25 = meningococcal strains 6 & 25

Meningococcal growth was inhibited at ANS concentrations of 0.25 mg/ml or higher when no hemoglobin was present. When 1% hemoglobin was incorporated, meningococci grew in the presence of all ANS concentrations. Similar reactions were observed with gonococci. The gonococci grew at ANS concentrations of 0.30 mg/ml or less when 1% hemoglobin was present but was inhibited by all ANS concentrations (in this experiment) when hemoglobin was not present.

As shown earlier, when no hemoglobin was present, an ANS concentration of 0.08 mg/ml was sufficient to differentiate the two pathogenic Neisseria. If 1% hemoglobin was incorporated, an ANS concentration of 0.5 mg/ml was required. It is felt that because of the additional nutritional growth factors supplied by the hemoglobin, more ANS is required to inhibit gonococcal growth and yet allow meningococci to grow. When hemoglobin is not incorporated, less ANS is necessary to inhibit gonococcal growth and yet allow meningococci to grow. Another explanation could be that hemoglobin binds the Ans, thus preventing it from acting on the bacteria. Accordingly, given the disclosures herein, it is clear that one skilled in the art can readily determine the quantity of ANS (or salt) sufficient to permit meningococci growth and inhibit gonococci growth in a given medium specific to those species of bacteria.

The TM-type medium containing at least about 0.50 mg/ml of ANS or salt thereof, preferably about 0.50 mg/ml, can be used in combination with other media to produce useful identification kits. Other specific media containing the requisite amount of ANS (or salt) can also be used in similar kits. For example, a media container with three sections can be prepared. One section for plain TM-type medium, a second section for TM-type medium containing about 0.5 mg/ml ANS salt, and a third section for a non-specific medium such as blood agar to isolate microbes other than gonococci or meningococci. Each of the three media can then be inoculated with a portion of the clinical specimen. Following incubation (e.g. 16–18 hr.), growth reactions on these media, together with the results of a Gram stain and an oxidase test (which can be performed on growth on the plain TM medium), would provide a definitive identification of *N. gonorrhoeae* or of *N. meningitidis*. Additional incubation time would not be required.

It can be appreciated that, given this disclosure, other media combinations will become apparent to those skilled in the art. Hence, it is intended that the above examples should be construed as illustrative only and that the scope of the present invention should be limited only by the following claims.

We claim:

1. A microbial growth medium specific to gonococci and meningococci bacteria, the medium having incorporated therein 8-anilino-1-naphthalene-sulfonic acid or a salt thereof in a quantity sufficient to permit the growth of meningococci bacteria and inhibit the growth of gonococci bacteria, the amount of 8-anilino-1-naphthalene-sulfonic acid or a salt thereof being at least about 0.08 mg./ml. of medium.

2. The medium of claim 1 wherein the medium comprises a Thayer-Martin medium containing at least about 0.5 mg of 8-anilino-1-naphthalene-sulfonic acid, or a salt thereof, per ml of medium.

3. The medium of claim 1 wherein the medium comprises a New York City medium containing at least about 0.08 mg of 8-anilino-1-naphthalene-sulfonic acid or a salt thereof per ml of medium.

4. The medium of claim 1 wherein the 8-anilino-1-naphthalene-sulfonic acid is present as a salt.

5. A method for the definitive identification of *Neisseria gonorrhoeae* in a specimen, the method comprising the steps of:
   A. incubating one portion of the specimen with a microbial growth medium specific to gonococci and meningococci bacteria; and
   B. incubating another portion of the specimen with a microbial growth medium specific to gonococci and meningococci bacteria and containing 8-anilino-1-naphthalene-sulfonic acid, or a salt thereof, in an amount sufficient to permit the growth of meningococci bacteria and inhibit the growth of gonococci bacteria.

6. The method of claim 5 wherein the medium of step (B) comprises a Thayer-Martin medium containing at least about 0.5% 8-anilino-1-naphthalene-sulfonic acid or a salt thereof.

7. The method of claim 5 wherein the medium of step (B) comprises a New York City medium containing at least about 0.08 mg of 8-anilino-1-naphthalene-sulfonc acid or a salt thereof per ml of medium.

8. The method of claim 5 wherein the incubation period of step (A) is for at least about 16–18 hours.

9. The method of claim 5 wherein the incubation period of step (B) is for at least 8 to 48 hours.

10. The method of claim 5 wherein the 8-anilino-1-naphthalene-sulfonic acid is present as a salt.

* * * * *

UNITED STATES PATENT AND TRADEMARK OFFICE
CERTIFICATE OF CORRECTION

PATENT NO. : 4,039,387
DATED : August 2, 1977
INVENTOR(S) : Lynn B. Simpson and Milton M. Takeguchi It is certified that error appears in the above-identified patent and that said Letters Patent are hereby corrected as shown below:

Column 4, line 5, "growth" should be -- growth-no growth --.

Column 4, line 49, "waS" should be -- was --.

Column 6, line 47, "Ans," should be -- ANS, --.

Signed and Sealed this

Twentieth Day of December 1977

[SEAL]

Attest:

RUTH C. MASON
Attesting Officer

LUTRELLE F. PARKER
Acting Commissioner of Patents and Trademarks